US008551958B2

(12) United States Patent
Rimoli et al.

(10) Patent No.: US 8,551,958 B2
(45) Date of Patent: Oct. 8, 2013

(54) GALACTOSYLATED PRO-DRUGS OF NON-STEROIDAL ANTI-INFLAMMATORIES WITH IMPROVED PHARMACOKINETIC CHARACTERISTICS AND REDUCED TOXICITY OF THE STARTING DRUG

(75) Inventors: Maria Grazia Rimoli, Giugliano (IT); Antonio Calignano, Naples (IT); Rosario Cuomo, Caserta (IT); Gianpiero Boatto, Sassari (IT); Enrico Abignente, Naples (IT); Daniela Melisi, Taranto (IT); Annalisa Curcio, Torre Annunziata (IT); Elvira Luongo, Torre le Nocelle (IT); Giovanna La Rana, Naples (IT); Oscar Sasso, Marigliano (IT); Giovanni Sarnelli, Pozzuoli (IT); Roberto Russo, Naples (IT); Maria Nieddu, Sassari (IT); Carla Cirillo, Orta di Atella (IT); Salvatore De Lucia, Forchia (IT)

(73) Assignees: Stewart Italia Srl, Milan (IT); Maria Grazia Rimoli, Giugliano (IT); Antonio Calignano, Naples (IT); Rosario Cuomo, Caserta (IT); Gianpiero Boatto, Sassari (IT)

( * ) Notice: Subject to any disclaimer, the term of this patent is extended or adjusted under 35 U.S.C. 154(b) by 197 days.

(21) Appl. No.: 13/015,980

(22) Filed: Jan. 28, 2011

(65) Prior Publication Data
US 2011/0212904 A1 Sep. 1, 2011

(30) Foreign Application Priority Data
Jul. 29, 2008 (IT) .............................. NA2008A0047

(51) Int. Cl.
*A61K 31/7024* (2006.01)
*C07H 13/02* (2006.01)
*C07H 13/04* (2006.01)
*C07H 13/08* (2006.01)
*C07H 13/10* (2006.01)

(52) U.S. Cl.
CPC ............ *A61K 31/7024* (2013.01); *C07H 13/02* (2013.01); *C07H 13/04* (2013.01); *C07H 13/08* (2013.01); *C07H 13/10* (2013.01)
USPC .............................. 514/23; 536/18.7; 536/119

(58) Field of Classification Search
None
See application file for complete search history.

(56) References Cited

U.S. PATENT DOCUMENTS

| 6,255,297 | B1 | 7/2001 | Dalko et al. | |
|---|---|---|---|---|
| 2005/0215487 | A1 | 9/2005 | Holick et al. | |
| 2011/0263712 | A1* | 10/2011 | Gore et al. | 514/575 |

FOREIGN PATENT DOCUMENTS

| CN | 1513861 A | | 7/2004 | |
|---|---|---|---|---|
| CS | 261333 | * | 10/1987 | ........... C07D 209/32 |
| FR | 1453 M | * | 8/1962 | |
| WO | 98/35973 A | | 8/1998 | |
| WO | 2004/002457 A2 | | 1/2004 | |
| WO | 2004/032971 A1 | | 4/2004 | |

OTHER PUBLICATIONS

FDA label for Ansaid® (Flubiprofen) revised Jul. 2005, pp. 1-19.*
Swart et al., "Synthesis and transdermal penetration of NSAID glycoside esters" International Journal of PHarmaceutics (2005) vol. 301 pp. 71-79.*
Certified Englsh translation of CS261333 above, published Oct. 1987, pp. 1-6.*
Hanessian S. et al: "One-step stereocontrolled synthesis of [alpha]-anomeric carboxylic acid esters from unprotected glycosyl donors; A water-soluble aspirin pro-drug analogue" Synthesis 2002 Georg Thieme Verlag DE, No. 14, 2002, pp. 1959-1968, p. 1962, Compound 11.
Zhao et al: "A facile enzymatic process for the preparation of ibuprofen ester prodrug in organic media", Journal of Molecular Catalysis. B, Enzymatic, Elsevier, Amsterdam, NL, vol. 36, No. 1-6, Nov. 1, 2005, pp. 47-53, ISSN: 1381-1177, the whole document, p. 48; figure SCHEMI 1.
Zhao X et al.: "Pharmacological activity and hydrolysis behavior of novel ibuprofen glucopyranoside conjugates", European Journal of Medicinal Chemistry, Editions Scientifique Elsevier, Paris, FR, vol. 41, No. 11, Nov. 1, 2006, pp. 1352-1358, ISSN: 0223-5234, [retrieved on Nov. 1, 2006], the whole document, p. 1353; figure SCHEME1.
Wang et al.: "Regioselective Enzymatic Synthesis of Non=Steroidal Anti-Inflammatory Drug Containing Glucose in Organic Media", Biotechnilogy Letters, Kluwer Academic Publishers, DO, vol. 27, No. 11, Jun. 1, 2005, pp. 789-792, ISSN: 1573-6776, the whole document, p. 790; figure SCHEME1.
Mishra A. et al.: "Synthesis , characterization and pharmacological evaluation of amide prodrugs of ketorolac", Eurpoean Joounal of Medicinal Chemistry, vol. 43, No. 11, Sep. 26, 2007, pp. 2464-2472, ISSN: 0223-5234, Abstract.

(Continued)

*Primary Examiner* — Eric S Olson
(74) *Attorney, Agent, or Firm* — Young & Thompson

(57) ABSTRACT

Pro-drugs of all non-steroidal anti-inflammatories with free acid function derivatized with an ester group, which have the general structural formula given below (I) where A is: aspirin, diflunisal, benorylate, ibufenac, diclofenac, indomethacin, sulindac, ketorolac, ibuprofen, naproxen, ketoprofen, fenoprofen, flurbiprofen, mefenamic acid, meclof enamic acid, flufenamic acid, niflumic acid, and where in the ester group R can be a sugar (amongst which aldose, or ketose pentose, or esose selected from a group of D- and L-enantioiuers of ribose, glucose, galactose, mannose, arabinose, xilose, allose, altrose, gulose, idose and talose and substituted derivatives thereof, such as glucosamine, galactosamine, N-acetyl glucosamine, N-acetyl galactosamine, N-acetyl ribosamine), a disaccharide, a trisaccharide or an oligosaccharide.

10 Claims, 7 Drawing Sheets

(56) References Cited

OTHER PUBLICATIONS

Tsunematsu H. et al.: "Synthesis and the Stereoselective Enzymatic Hydrolysis of Flurbiprofen-basic Amino Acid Ethyl Esters" Jounal of Drug Targeting, Harwood Academic Publishers GMBH, DE, vol. 2, No. 6, Jan. 1, 1995, pp. 517-525, ISSN: 1061-186X, the whole document, figure 1.

Curcio A. et al.: "Galactosyl prodrug of ketorolac: synthesis, stability, and pharmacological and pharmacokinetic evaluations." Journal of Medicinal Chemistry Jun. 25, 2009, vol. 52, No. 12, pp. 3794-3800, ISSN: 1520-4804.

Bonina F. P et al.: "Pharmacokinetic and pharmacodynamic profile of triethylene glycol indomethacin ester as a new oral prodrug" Journal of Controlled Release, Elsevier, Amsterdam, NL, Sep. 1, 1996, pp. 187-193, ISSN: 0168-3659.

Bonina F. et al.: "Synthesis and in vitro chemical and enzymatic stability of glycosyl 3'-azido-3-deoxythymidine derivatives as potential anti-HIV agents", European Journal of Pharmaceutical Sciences 2002 Elsevier NL, vol. 16, No. 3 2002, pp. 167-174.

Bonina F. et al.: "Glycosyl derivatives of dopamine and L-dopa as anti-Parkinson prodrugs: synthesis, pharmacological activity and in vitro stability studies", Jounral of Drug Targeting, Harwood Academic Publishers GMBH, DE, vol. 11, No. 1, Jan. 1, 2003, pp. 25-36, ISSN: 1061-186X.

International Search Report, dated Mar. 24, 2010, from corresponding PCT application.

* cited by examiner

GALACTOSYLATED PRO-DRUGS OF NON-STEROIDAL ANTI-INFLAMMATORIES WITH IMPROVED PHARMACOKINETIC CHARACTERISTICS AND REDUCED TOXICITY OF THE STARTING DRUG

The present invention relates to galactosylated pro-drugs of non-steroidal anti-inflammatories with free acid function and the process of synthesis thereof, which enables minimization of the gastrointestinal toxicity of the starting anti-inflammatory by means of esterification of its carboxylic group.

Forming part of non-steroidal anti-inflammatory drugs with free acid function are: aspirin, aceclofenac, acemetacin, diflunisal, benorylate, ibufenac, diclofenac, indomethacin, sulindac, ketorolac, ibuprofen, naproxen, ketoprofen, fenoprofen, flurbiprofen, mefenamic acid, meclofenamic acid, flufenamic acid, niflumic acid.

Forming a further subject of the invention are pro-drugs of non-steroidal anti-inflammatories with free acid function derivatized with an ester group that have the general structural formula given below:

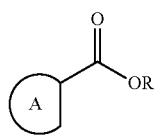

(I)

where A is: aceclofenac, acemetacin, aspirin, dexketoprofen, diflunisal, etodolac, benorylate, ibufenac, diclofenac, indomethacin, fenbufene, sulindac, ketorolac, ibuprofen, naproxen, ketoprofen, fenoprofen, flurbiprofen, mefenamic acid, meclofenamic acid, flufenamic acid, niflumic acid, tiaprofenic acid; and where in the ester group R can be a sugar (amongst which aldose, or ketose pentose, or esose, selected from a group of D- and L-enantiomers of ribose, glucose, galactose, mannose, arabinose, xilose, allose, altrose, gulose, idose and talose and substituted derivatives thereof, such as glucosamine, galactosamine, N-acetyl glucosamine, N-acetyl galactosamine, N-acetyl ribosamine), a disaccharide, a trisaccharide, or an oligosaccharide:

where by disaccharide is meant a polymeric assemblage of two sugars to constitute both homopolymers (maltose and cellobiose) and heteropolymers (lactose and sucrose);

where by trisaccharide is meant a polymeric assemblage of three sugars;

where by oligosaccharides are meant polymers constituted by 4 to 10 residues; the polymer can be either homosaccharidic (the same sugar that repeats) or heterosaccharidic (various sugars); and where the sugars are each bound to one another via a glycoside bond between C1 and C4 or alternatively between C1 and C3 or else between C1 and C6.

The ensuing description refers to some examples of embodiment for which both synthesis and clinical and pharmacological tests were carried out in order to evaluate the anti-inflammatory, analgesic, and ulcerogenic activities of the pro-drug.

In particular, attention has been paid to the galactosylated derivative of ketorolac (hereinafter referred to as Ketogal):

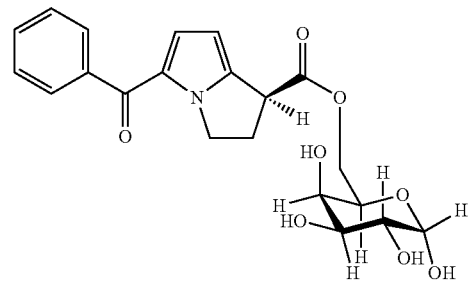

(II)

Said derivative is a pro-drug designed to overcome the obstacles, of a pharmacokinetic and pharmacological type, which render clinical use of ketorolac difficult, such as low oral availability, chemical instability, and toxicity at a gastrointestinal level.[1-4]

As is known, pro-drugs are inert derivatives constituted by an active principle, bound chemically and in a reversible way to which is a vehicle group. In the embodiment according to the present invention that will be provided hereinafter, the drug is represented by ketorolac, the general structural formula of which is:

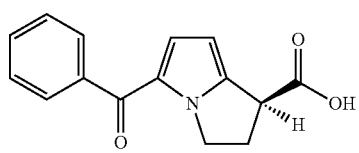

1 and the vehicle is represented by a galactose molecule.

Ketogal is synthetized by esterifying the carboxyl group of ketorolac with the hydroxyl in position 6' of galactose.

According to the invention, the compound is synthetized by means of a reaction of esterification between ketorolac and 1,2,3,4-di-O-isopropylidene-D-α-galactopyranose using N-ethyl-N'-(3-dimethyl aminopropyl)carbodiimide (EDC) hydrochloride as condensing agent, and 4-(dimethyl amino) pyridine (DMAP) as catalyst, in anhydrous dichloromethane:

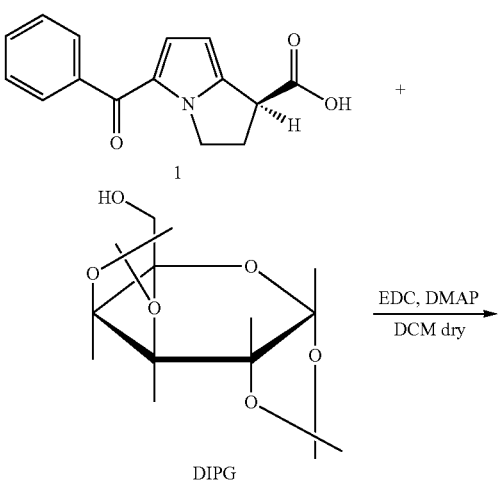

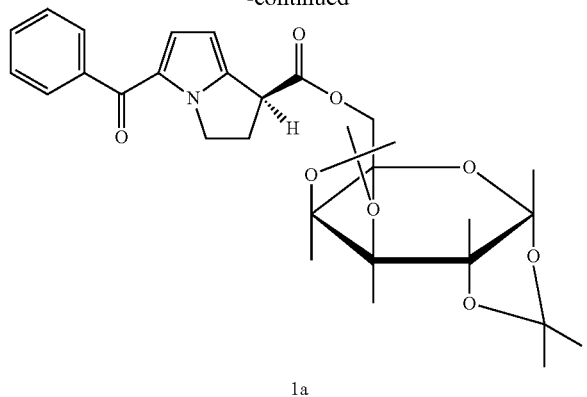

1a

The protected conjugate, 1a, is thus obtained with a yield of 75%. The ketals are completely removed by means of trifluoroacetic acid (TFA) in anhydrous dichloromethane so as to obtain Ketogal, with a yield of 65%

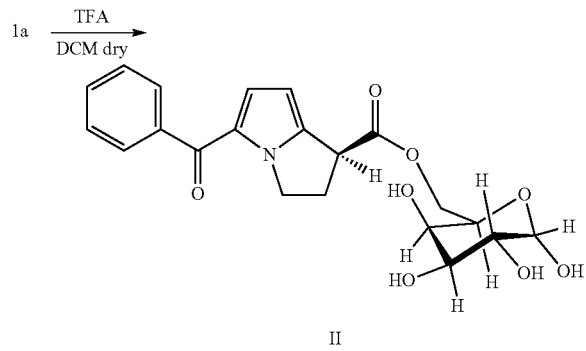

II

The chemical stability of the pro-drug was measured both at pH 1 and pH 7.4 so as to verify its degree of manageability and the possibility of oral administration. The enzymatic stability was also measured, in plasma, with the purpose of ascertaining the reactivity of the pro-drug in an environment as close as possible to the biological one (FIG. 1).

From studies on gastrolesivity and pharmacokinetics, Ketogal has shown that it does not cause ulcers and has a better oral availability than ketorolac. Finally, studies of pharmacological activity have shown that Ketogal (0.163 mg/kg) has a better analgesic and anti-inflammatory activity than ketorolac (0.1 mg/kg), both after oral administration and after subcutaneous administration.

Further characteristics and advantages of the invention will emerge clearly from the ensuing detailed description and from the corresponding experimentation of some embodiments, with reference to the annexed plates of drawings, wherein.

Figure 8:
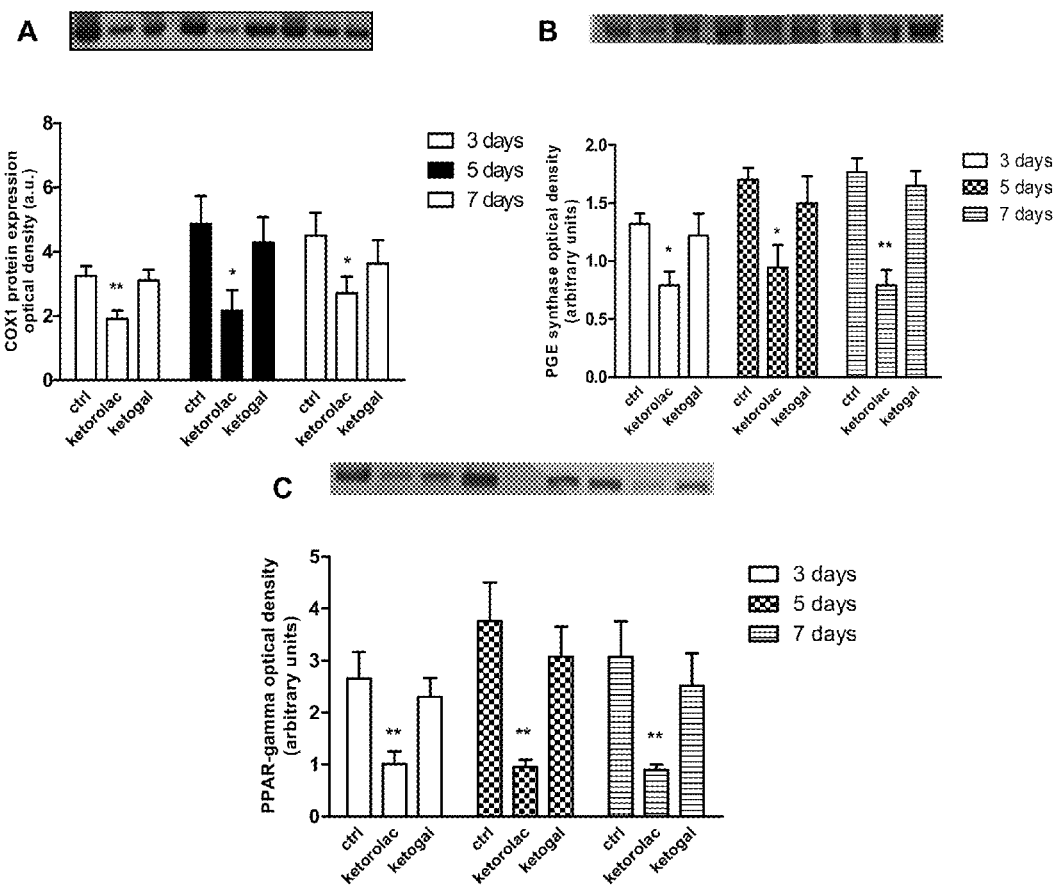

FIG. 8 presents Western blots analysis results for (A) COX-1, (B) PGE synthase and (C) PPAR-gamma protein expression in the stomach of mice treated with vehicle, ketorolac or ketogal for 3, 5 and 7 days.

Figure 9:
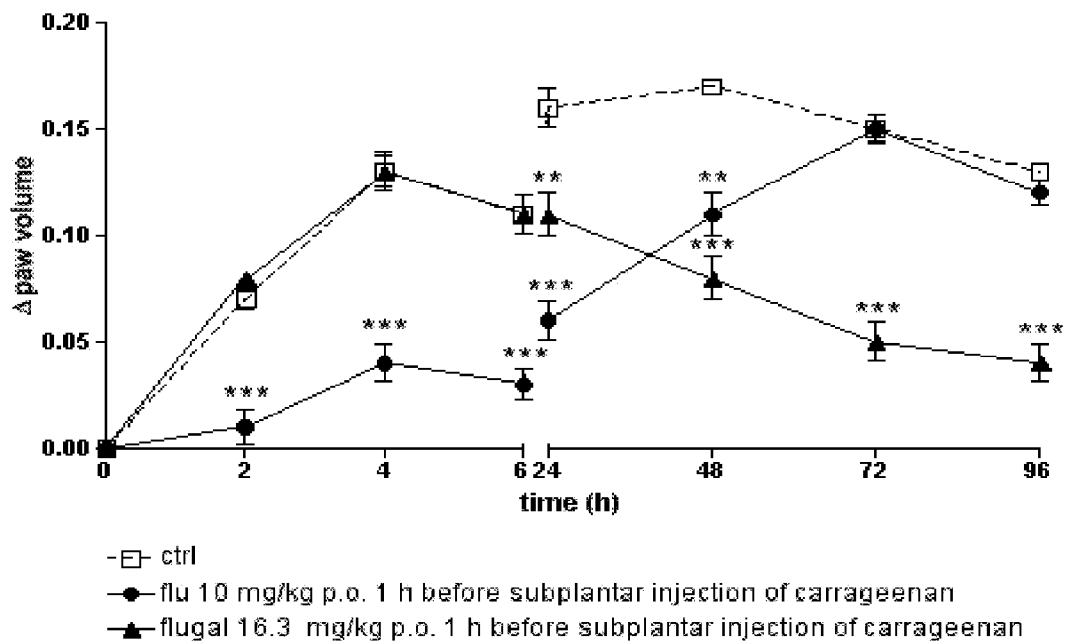

FIG. 9 shows the anti-inflammatory effect of oral administration of flurbiprofen (10 mg/kg) and flugal (16.3 mg/kg) on mouse carrageenan paw oedema.

Figure 10:
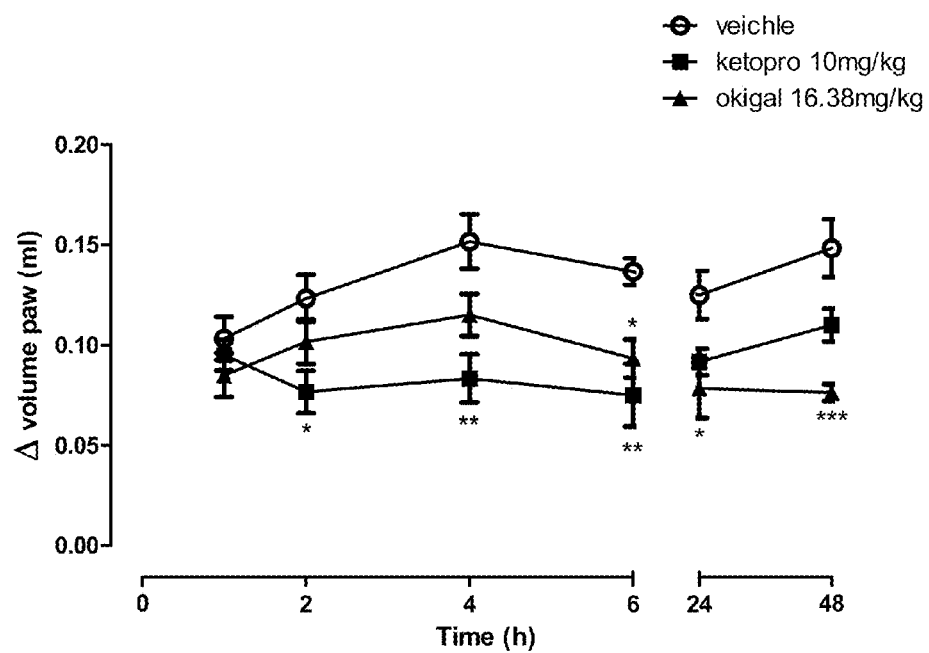

FIG. 10 shows the anti-inflammatory effect of oral administration of ketoprofen (10 mg/kg) and okigal (16.3 mg/kg) on mouse carrageenan paw oedema.

CHEMICAL PART

Synthesis of Diacetone 6'-O-ketorolac-D-galactopyranoside (1a)

1 g of ketorolac 1 (3.9 mmol), 1.015 g of 1,2,3,4-di-O-isopropylidene-D-α-galactopyranose (3.9 mmol), 748 mg of N-ethyl-N'-(3-dimethyl aminopropyl)carbodiimide (EDC) HCl (3.9 mmol) and 24 mg of 4-(dimethyl amino)pyridine (DMAP) (0.19 mmol) were dissolved in anhydrous dichloromethane (10 mL). The reaction mixture was kept under electromagnetic stirring at room temperature for 12 hours. The organic phase was extracted several times with water and dehydrated with anhydrous sodium sulphate, filtered, and dried in vacuo. The reaction crude was purified on a chromatography column with silica gel using as eluent $CHCl_3$, to obtain 1.45 g of 1a as a white solid (yield 75%).

$^1$H-NMR ($CDCl_3$): δ 1.30, 1.31, 1.40, 1.41 (4 s, 12H, ketals); 2.80, 2.90 (m, 2H, 2-H); 3.30 (m, 1H, 1-H); 4.05 (m, 1H, 4'-H); 4.15 (m, 1H, 5'-H); 4.20 (m, 2H, 6'-H); 4.40 (m, 1H, 2'-H); 4.50 (m, 1H, 3'-H); 4.60 (m, 2H, 3-H); 5.35 (m, 1H, 1'-H); 5.90 (d, 1H, 7-H); 6.80 (d, 1H, 6-H); 7.45 (m, 2H, 2,6-Ph); 7.55 (m, 1H, 4-Ph); 7.85 (m, 2H, 3,5-Ph). $^{13}$C-NMR ($CDCl_3$): δ 20 and 22 (4-$CH_3$-ketals); 30 (C-2); 44 (C-3); 48 (C-1); 65 (C-6'); 66.7 (C-4'); 71 (C-5'); 71.5 (C-2'); 72 (C-3'); 97 (C-1'); 105 (C-7); 109 and 111 (C-ketals); 125 (C-6); 127 (C-5); 129 (3,5-Ph); 130 (2,6-Ph); 133 (4-Ph); 140 (C-8); 142 (1-Ph); 175 (ketonic CO); 185 (esteric CO). m/z: 498 $(M+H)^+$.

Synthesis of ketorolac-D-galactos-6'-yl ester (Ketogal)

Added to a solution of 1a (1.45 g; 2.9 mmol) in anhydrous dichloromethane (10 mL) were 2 mL of trifluoroacetic acid (TFA), and the reaction mixture was kept under electromagnetic stirring at room temperature for 48 hours. By evaporating the solvent, a residue was obtained, which was purified on a chromatography column with silica gel using as eluent $CHCl_3$ in a gradient of $CH_3OH$ to obtain 800 mg of Ketogal as a white solid (yield 65%). mp: 195 C. $^1$H-NMR ($CD_3OD$): δ 2.85 (m, 2H, 2-H); 3.50 (m, 1H, 1-H); 3.75 (m, 1H, 4'-H); 3.85 (m, 1H, 5'-H); 4.20 (m, 2H, 6'-H); 4.30 (m, 1H, 2'-H); 4.35 (m, 1H, 3'-H); 4.50 (m, 2H, 3-H); 5.15 (m, 1H, 1'-H); 6.15 (d, 1H, 7-H); 6.80 (d, 1H, 6-H); 7.45 (m, 2H, 2,6-Ph); 7.55 (m, 1H, 4-Ph); 7.75 (m, 2H, 3,5-Ph). $^{13}$C-NMR ($CD_3OD$): δ 30 (C-2); 44 (C-3); 48 (C-1); 65.5 (C-6'); 68 (C-4'); 70 (C-5'); 73.1

(C-2'); 74.9 (C-3'); 94 and 99 (C-1'); 105 (C-7); 125 (C-6); 127 (C-5); 129 (3,5-Ph); 130 (2,6-Ph); 133 (4-Ph); 140 (C-8); 142 (1-Ph); 175 (ketonic CO); 185 (esteric CO). m/z: 418 $(M+H)^+$.

Stability Studies on Ketogal

For the stability study, the solutions of pro-drug were prepared by dissolving an aliquot of Ketogal in a phosphate buffer at pH 7.4, or else in a solution of HCl 0.1 N (pH 1), as regards chemical stability, or else in a plasma specimen, for enzymatic stability. The solutions were kept in the dark, at a temperature of 37° C., for 24 hours. After each hour an aliquot of specimen was taken. In the case of plasma, said aliquot was previously extracted with acetonitrile (1:2), "vortexed" and centrifuged at 3000 r.p.m. for 10 min. The supernatant was taken and used for analysis at HPLC with diode detector. The half-lives for chemical stability and enzymatic stability were calculated by quantizing, in time, the percentage of pro-drug that remained in solution. For the chromatographic separations, a 1090L HPLC (Hewlett-Packard, Palo Alto, USA) was used, coupled to a diode detector HP 1040A. A Phenomenex Luna C18 (250×4.6 mm, 5 µm) column was used. The wavelength used was 313 nm. The mobile phase was constituted by acetonitrile and an aqueous solution of phosphoric acid 1 mm (pH 3) in the ratio of 68:32. The flow was 1 mL/min, with an injection volume of 20 µl. All the reagents and the solvents used were of analytical degree. The distilled and deionized water was purified by means of a Milli Q system (Millipore). The retention times of the compounds were: ketorolac: 6.7 min; Ketogal: 3.8 min. As internal standard tolmetin was used (9.3 min). The straight line of calibration for quantification of the compounds was constructed using standard solutions with concentrations of between 0.1 and 100 µg/ml. The linearity was obtained with a coefficient of regression ($R^2$) of approximately 0.998.

From the results obtained, illustrated in Table 1, it is possible to envisage for Ketogal a good stability, which also enables administration thereof by oral route. In this way, ketorolac will not be released fast at a gastric level, causing the classic side effects, and may perform its pharmacological action once the circulatory system has been reached.

TABLE 1

Chemical stability and enzymatic stability of Ketogal

| COMPOUND | pH 7.4 T½ (HOURS) | pH 1 T½ (HOURS) | Plasma T½ (HOURS) |
| --- | --- | --- | --- |
| Ketogal | >4 | 2.1 | 1.5 |

Pharmacological Part

All the tests were conducted in due respect to the Italian guidelines (D.L. [Order of the Executive] No. 116 of Jan. 27, 1992) and of the European Community (Directive of Nov. 24, 1986, 86/609/ECC). All the surgical procedures were approved by the Ministry for Scientific Research and were in compliance with the "International Association for the Study of Pain".

Test 1—Ulcerogenicity Studies

The gastric lesions were evaluated in male Swiss mice. To the fasted animals (16-18 h) were administered, by oral route, ketorolac (10 mg/kg), Ketogal (16.3 mg/kg), or the vehicle. After 4 hours, the mice were sacrificed and the stomach removed, cut along the major curvature, washed with physiological solution, and the mucous was examined for evaluation of the presence of petechias and/or gastric lesions. A "score" of 1 was assigned to the petechias, and a "score" based on the diameter (a "score" of 5 for lesions of a diameter of less than 1 mm; a "score" of 10 for lesions with a diameter of more than 1 mm) was, instead, assigned to the lesions.

The study of the ulcerogenic activity showed for Ketogal a clear reduction in the gastrolesive properties, as compared to ketorolac, following upon equimolar administration of the two compounds; in fact Ketogal showed only a slight irritation of the gastric mucosa, with an almost total absence of ulcers (Table 2).

TABLE 2

Ulcerogenicity

| Compound | Oral dose (mg/kg) | Number of ulcers | Degree of ulcerogenicity |
| --- | --- | --- | --- |
| Control (CMC 0.5%) | — | 0 | — |
| ketorolac | 10.0 | 4 ± 0.4 | 10 |
| Ketogal | 16.3 | 1 ± 0.4 | 1 |

Test 2—Pharmacokinetic Studies

The pharmacokinetic profile of Ketogal and of ketorolac was evaluated in Wistar rats by measuring the concentration of the two compounds in the plasma, in the stomach, in the kidney, and in the liver. The rats received ketorolac (0.100 mg/kg) or Ketogal (0.163 mg/kg) by oral route and were sacrificed after 1 h, 2 h, 4 h, and 6 h from administration. The various specimens were treated with acetonitrile, and the suspension was "vortexed" and centrifuged at 3000 r.p.m. for 10 min. The organic phase was injected in the same HPLC system used for the stability assays. The results are given in FIGS. 2A and 2B.

Figure 1:
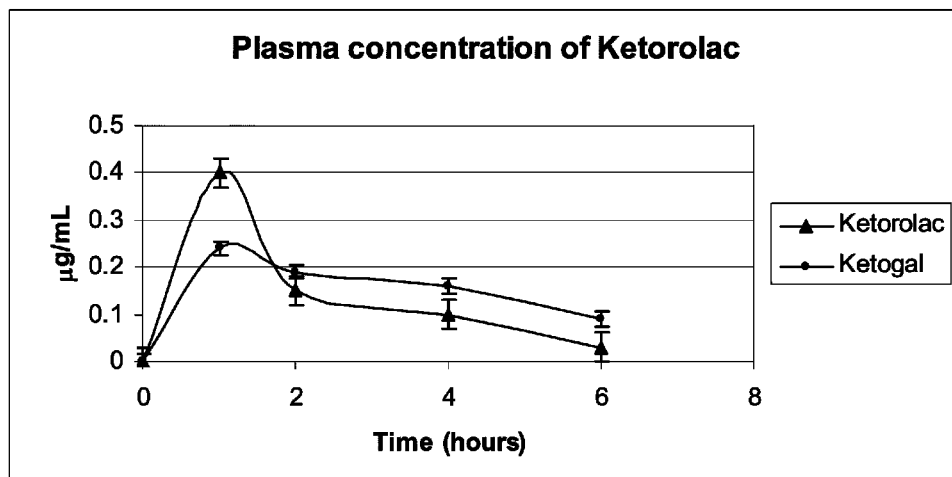
FIG. 1 shows the plasmatic concentration of ketorolac after administration of Ketogal and ketorolac as such.
Figure 2A:
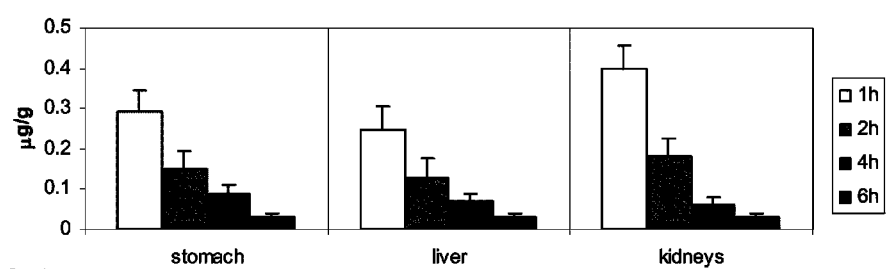
FIGS. 2A and 2B show the concentration of ketorolac in the stomach, liver, and kidneys after administration of ketorolac as such (A) and of Ketogal (B)
Figure 2B:
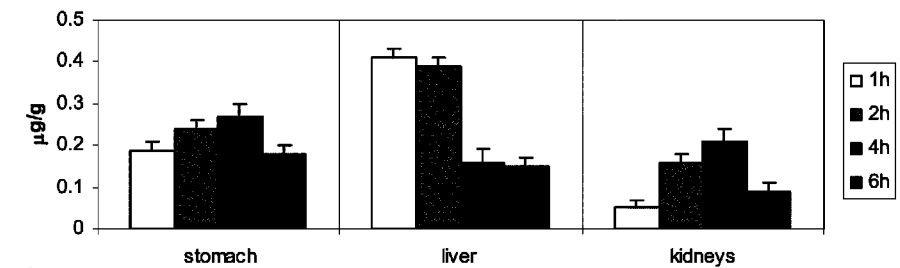

From the results obtained it emerged that the introduction of galactose increased the oral availability of ketorolac. In fact, the plasma levels of the drug, following upon administration of Ketogal, were higher than the ones observed following upon administration of the drug as such (FIG. 1). In the plasma, moreover, the pro-drug was not present, which is indicative of the fact that hydrolysis occurs at a gastric level. In the stomach, in fact, (FIGS. 2A and 2B) it is evident how Ketogal (FIG. 2B) hydrolyses progressively, releasing ketorolac, the concentration of which remains roughly constant over time and even higher, after 2 hours, than the one obtained following upon administration of the drug as such. The kidney showed a profile similar to that of the stomach, with the difference that the greater concentration of ketorolac, after administration of Ketogal, was found after three hours, with respect to the administration of the drug as such (FIG. 2A). There were, moreover, no traces of the pro-drug.

Instead, in the liver (FIGS. 2A and 2B), Ketogal reappeared, which is sign of a likely entero-hepatic recycling of the pro-drug, and the concentration of ketorolac was always higher following upon administration of Ketogal (FIG. 2B) as compared to that of the drug alone (FIG. 2A).

Test 3—Analgesic Activity

The analgesic activity was studied using the "writhing test" using acetic acid and using magnesium sulphate. To the mice there was administered by intraperitoneal route 1 mL of solution at 1% of acetic acid, and the number of writhing events was evaluated for 20 min, after 5 min from administration of the solution of acetic acid. Writhing is defined as a contraction of the abdominal muscles accompanied by elongation of the body and of the rear legs. Ketorolac and Ketogal were administered by oral route 60 min prior to administration of the solution of acetic acid.

The analgesic effect is expressed in number of writhing events as compared to the control.

Figure 3A:
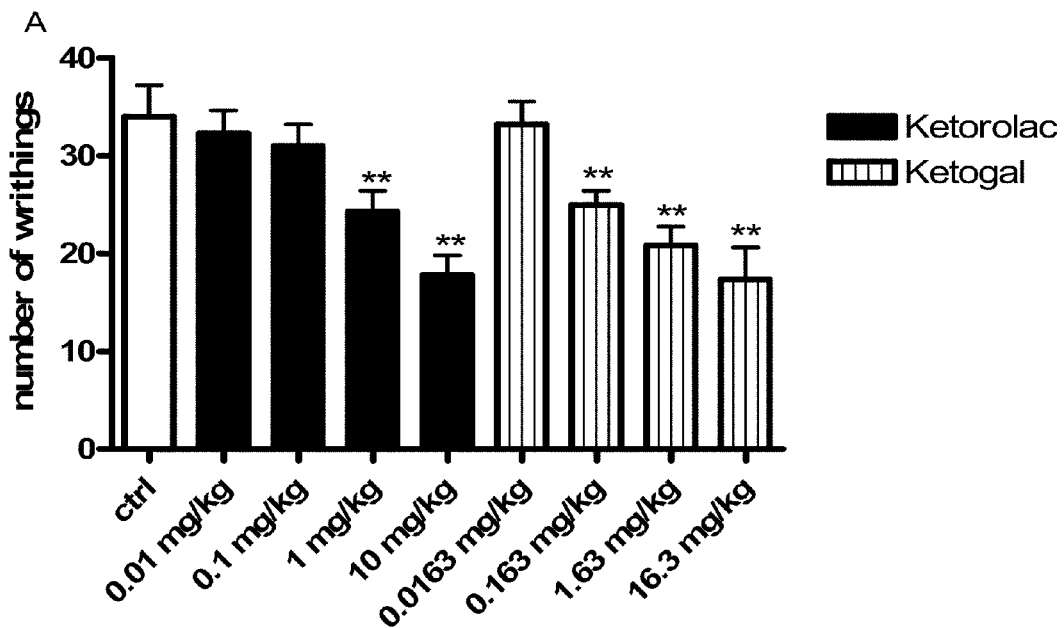
FIG. 3A shows the analgesic effect on writhing induced by acetic acid.

Ketorolac (0.01-10 mg/kg, by oral route) caused a dose-dependent analgesic effect. In particular, the effect was significant at the dosages of 1 and 10 mg/kg (p<0.01). Ketogal, (0.0163-16.3 mg/kg, by oral route) showed a dose-dependent analgesic effect of higher than 0.163 mg/kg (FIG. 3A).

Figure 3B:
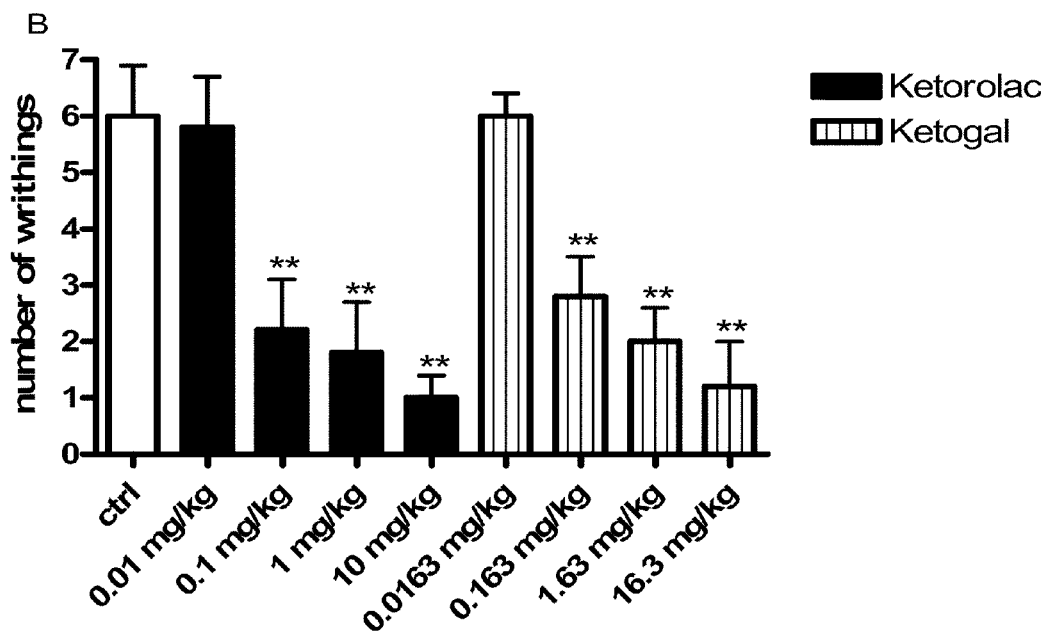
FIG. 3B shows the analgesic effect on writhing induced by magnesium sulphate.

In order to determine whether ketorolac and Ketogal are able to inhibit visceral pain, the effects of these compounds on "writhing" induced by magnesium sulphate were tested. Magnesium sulphate induces a reversible response when injected by intraperitoneal route in the mouse. The administration of 120 mg/kg of magnesium sulphate induces an average of 6±0.9 episodes of "writhing" in the mouse (n=6). Both ketorolac (0.01 to 10 mg/kg) and Ketogal (in equimolar dose as compared ketorolac) administered 1 hour before the magnesium sulphate are able to inhibit this response in a dose-dependent way (FIG. 3B).

Test 4—Anti-Inflammatory Activity

Anti-inflammatory activity was tested by means of the carrageenan oedema test. The mice were divided into groups of six. The initial volumes of the leg of all the animals were measured using a plethysmometer. The oedema is induced in the leg by means of sub-plantar injection of 50 μl of saline solution containing 1% of carrageenan. The volume of the leg was measured at different time intervals. Said experimental model consists of two phases: a first, acute, phase lasting 6 hours and a second, chronic, phase, up to 72 hours. Treatment with Ketogal (0.163-16.3 mg/kg oral), 1 h prior to injection of carrageenan, considerably reduces the oedema of the leg in a time-dependent and dose-dependent way.

Figure 4A:
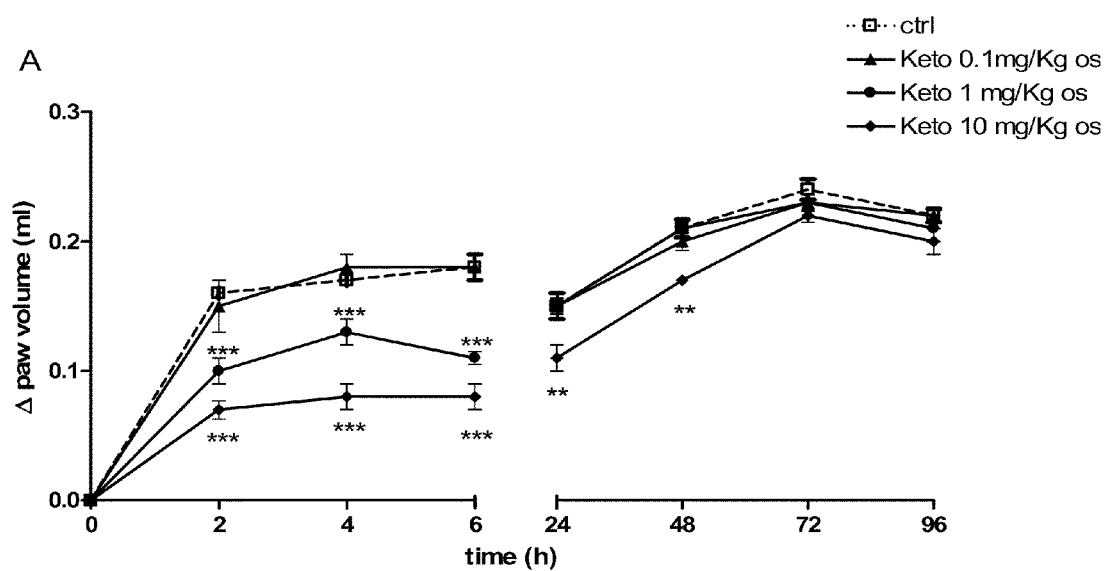
FIGS. 4A and 4B show the anti-inflammatory effect of the oral administration of ketorolac (A) and Ketogal (B).
Figure 4B:
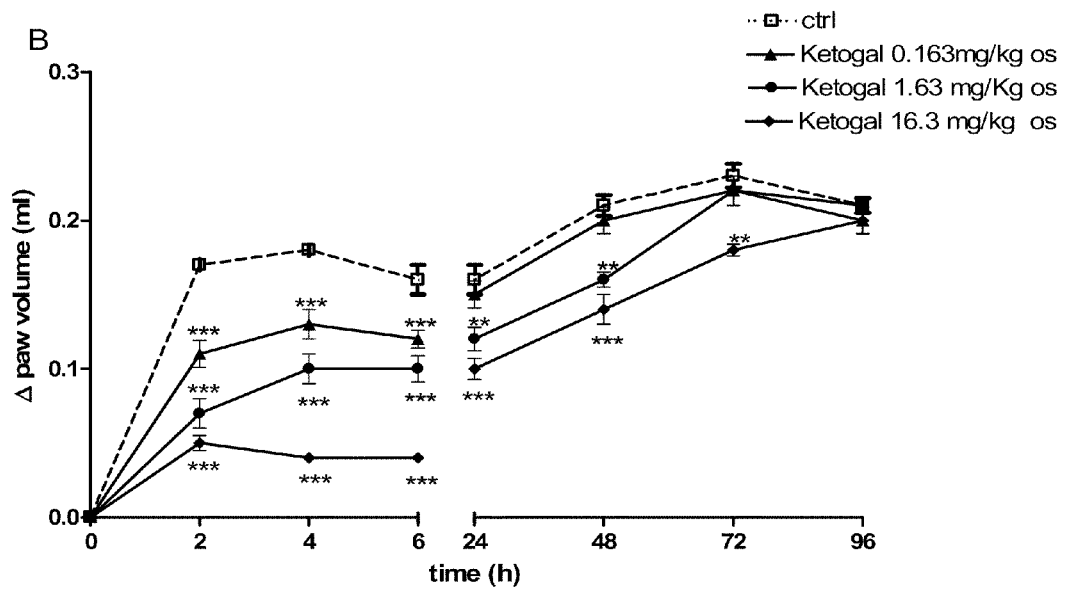

During the first phase, all the doses tested inhibited formation of oedema, whereas the lowest dose (0.1 mg/kg) of ketorolac had no effect. Finally, the effect of Ketogal continued also in the second phase. (FIGS. 4A and 4B).

Test 5—Pharmacological Tests on the Physical Mixture of Ketorolac and Galactose

The anti-inflammatory activity of the physical mixture of ketorolac and galactose was evaluated with the carrageenan induced mice hind paw edema assay, as described for ketogal.

Figure 5:
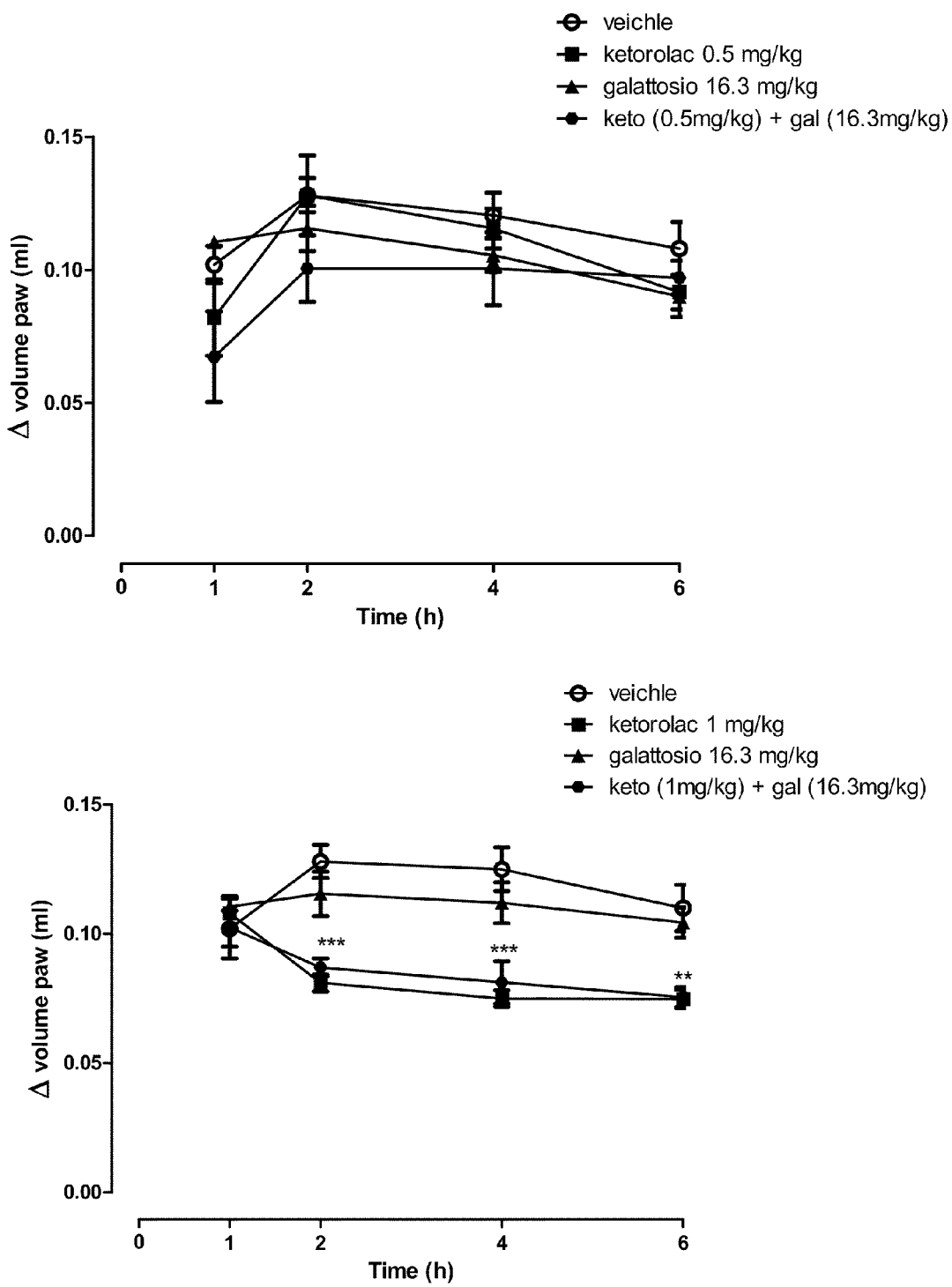
FIG. 5 shows the anti-inflammatory effect of oral administration of both ketorolac (0.5 mg/kg and 1 mg/kg) and galactose (16.3 mg/kg) on mouse carrageenan paw oedema.

Both ketorolac free acid (0.5 mg/kg and 1 mg/kg) and galactose (16.3 mg/kg) were orally administrated 1 h before carrageenan challenge. As shown in FIG. 5, there isn't any increase in the anti-inflammatory activity when galactose is administered at the same time of ketorolac, without the chemical link present in the prodrug ketogal. Furthermore, no anti-inflammatory activity is shown by galactose alone. So the esterification of ketorolac with galactose is crucial for the achieved results. Control animals were treated with CMC, flurbiprofen and flugal 1 h before subplantar injection of carrageenan. Data are expressed as mean values (SEM of six animals for each group: (*) p<0.001; () p<0.01 versus control group).

Test 6—Chronic and Sub-Chronic Experiments of Ketogal

In order to verify the suitability of ketogal after a long-term administration, further toxicological experiments were performed.

Chronic and sub-chronic experiments were carried out treating male Swiss mice with the highest doses of drugs (10 mg/Kg of ketorolac and 16.3 mg/Kg of ketogal), orally administrated, for 3, 5 and 7 days. Animals were sacrificed and then liver, stomach and kidney were collected in glass tubes and analysed histologically and biochemically.

Figure 6:
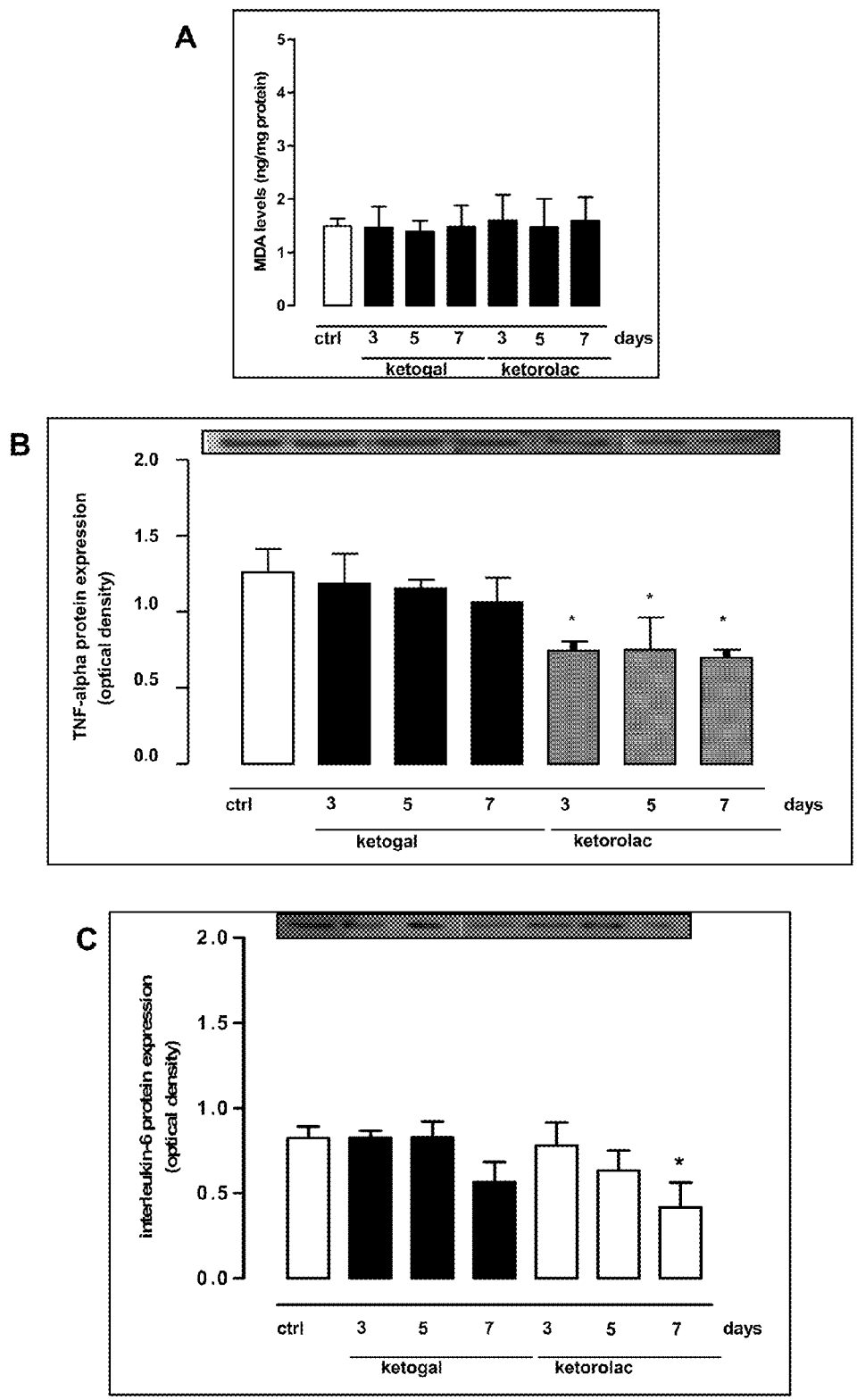
FIG. 6 depicts western blot analyses performed in liver lysates. (A) malonyldialdehyde assay; (B) TNF-alpha protein expression; (C) IL-6 protein expression.

Liver samples were fixed in 10% buffered formalin and embedded in paraffin, sliced, and stained with hematoxylin & eosin (H&E) for assessment of liver pathology. Mice treated with ketogal had normal liver histology compared to control mice: inflammation necrotic area, sinusoidal dilatation and congestion were absents. To confirm histological data, western blot analysis for TNF-alpha, IL-6 and malonyldialdehyde assay were then performed in liver lysates. Biochemical analysis confirm that ketogal-treated mice had no hepatic inflammation and/or damage, since TNF-alpha, IL-6 and lipid peroxidation levels were no different compared to control mice (FIG. 6).

Mice treated both with ketogal and ketorolac had normal kidney histology compared to control, after 3, 5 and 7 days.

Figure 7:
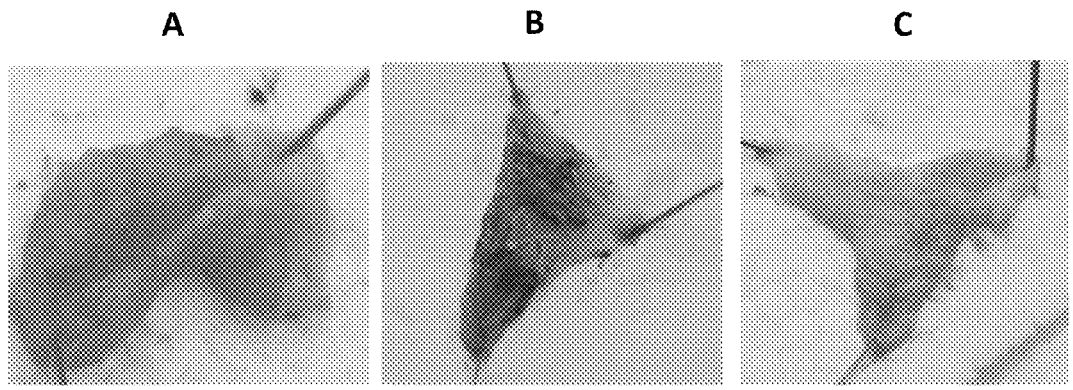
FIG. 7 shows stomach samples of mice: (A) control; (B) mice treated with ketorolac for 3 days; (C) mice treated with ketogal for 3 days.

Stomach samples of mice treated with ketorolac for 3 days had an high ulcerogenicity degree, whereas those treated with ketogal were undamaged and similar to control (FIG. 7).

FIG. 8 shows representative western blots for COX-1, PGE synthase and PPAR-gamma protein expression in the stomach of mice treated with vehicle, ketorolac or ketogal for 3, 5 and 7 days. Gastric COX-1 protein expression after both 3, 5 and 7 days resulted significantly inhibited compared to control stomachs. In parallel, also PGE synthase resulted significantly reduced in both 3, 5 and 7 days ketorolac-treated mice. Similarly, ketorolac significantly reduced PPAR-gamma protein expression in both 3, 5 and 7 days-treated mice. Very interestingly, in ketogal-treated mice, both COX-1, PGE synthase and PPAR-gamma protein expression was not inhibited after 3, 5 and 7 days.

Further Studies and Investigations

In order to broaden the study of the stability and of the possible applications of blocking of the carboxylic function of a starting drug, which seems to be responsible for its gastrolesivety, further examples of synthesis and characterization of other galactosylated derivatives are illustrated.

Synthesis of Flugal

The galactosylated derivative of flurbiprofen (Flugal)

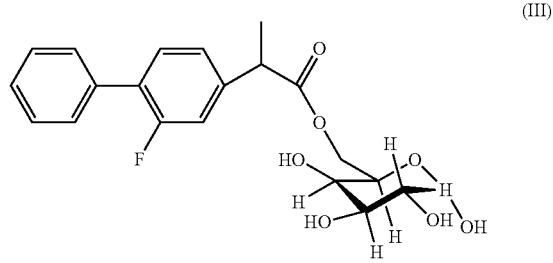

(III)

is a pro-drug in which the drug is represented by flurbiprofen

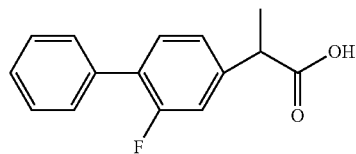

2 and the vehicle by a galactose molecule.

Flugal is synthetized by esterifying the carboxyl group of flurbiprofen with the hydroxyl in position 6' of galactose, as described above for Ketogal.

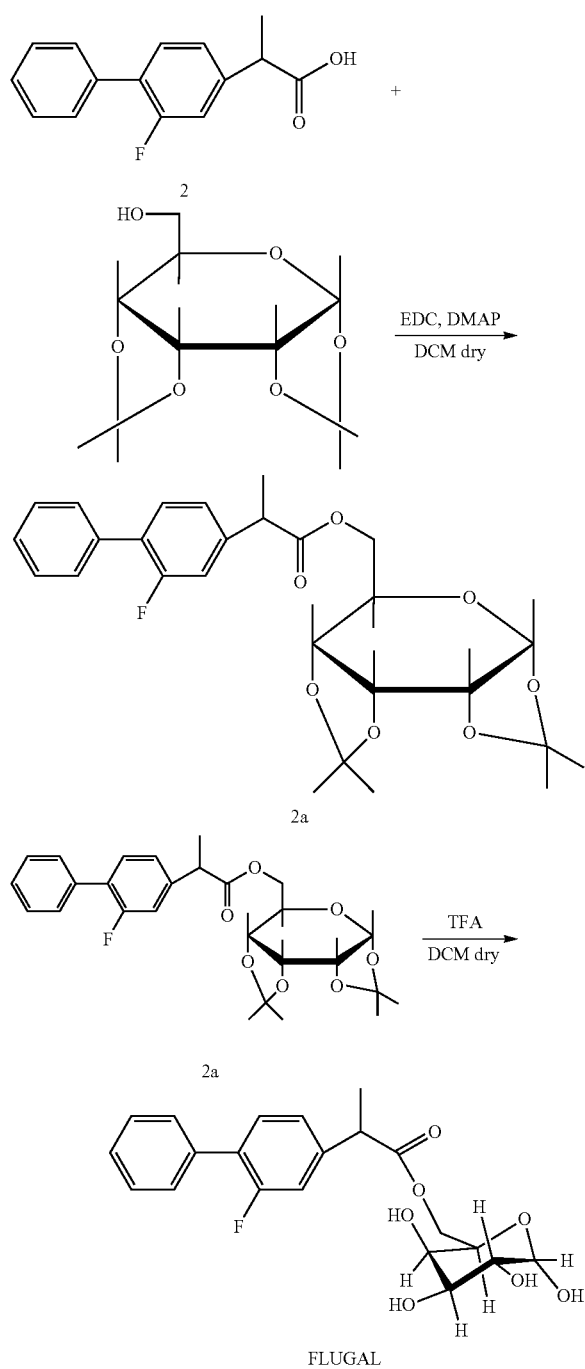

Synthesis of Diacetone 6'-O-Flurbiprofen-D-galactopyranoside (2a)

1 g of flurbiprofen 2 (4.1 mmol), 1.067 g of 1,2,3,4-di-O-isopropylidene-D-α-galactopyranose (4.1 mmol), 786 mg of N-ethyl-N'-(3-dimethyl aminopropyl)carbodiimide (EDC) HCl (4.1 mmol), and 25.2 mg of 4-(dimethyl amino)pyridine (DMAP) (0.205 mmol) were dissolved in anhydrous dichloromethane (10 mL). The reaction mixture was kept under electromagnetic stirring at room temperature for 12 hours. The organic phase was extracted several times with water and dehydrated with anhydrous sodium sulphate, filtered and dried in vacuo. The reaction crude was purified on a chromatography column with silica gel using $CH_2Cl_2$ as eluent, to obtain 1.21 g of 2a as a white solid (yield 61%) m/z: 487 $(M+H)^+$.

Synthesis of flurbiprofen-D-galactos-6'-yl ester (Flugal)

Added to a solution of 2a (1.21 g; 2.5 mmol) in anhydrous dichloromethane (10 mL) were 2 mL of trifluoroacetic acid (TFA), and the reaction mixture was kept under electromagnetic stirring at room temperature for 48 hours. By evaporating the solvent, a residue was obtained, which was purified on a chromatography column with silica gel using $CHCl_3$ as eluent in a gradient of $CH_3OH$ to obtain 538 mg of Flugal as a white solid (yield 53%).

$^1$H-NMR ($CD_3OD$): δ 1.5 (d, 3H, —$CH_3$); 3.45 (m, 1H, 4'-H); 3.70 (m, 1H, —CH); 3.8 (m, 1H, 5'-H); 4.20 (m, 2H, 6'-H); 4.30 (m, 1H, 2'-H); 4.40 (m, 1H, 3'-H); 5.15 (m, 1H, 1'-H); 7.17 (m, 2H, 6,5-Biph); 7.36 (m, 1H, 3-Biph); 7.43 (m, 3-H, 9,10,12-Biph); 7.52 (m, 2-H, 8,12-Biph). $^{13}$C-NMR ($CD_3OD$): δ 18 ($CH_3$); 45 (CH); 64 (C-6'); 68 (C-4'); 70 (C-5'); 73 (C-2'); 74 (C-3'); 93 and 98 (C-1'); 115 (3-Biph); 124 (5-Biph); 127 (10-Biph); 128 (8,12-Biph); 129 (9,11-Biph); 131 (6-Biph); 135 (4-Biph); 142 (7-Biph); 159 (1-Biph); 160 (2-Biph); 174 (esteric CO). m/z: 407 $(M+H)^+$.

Stability Studies on Flugal

For the study of the stability, the solutions of pro-drug were prepared by dissolving an aliquot of Flugal in a phosphate buffer at pH 7.4, as regards chemical stability, or else in a plasma specimen, for enzymatic stability. The solutions were kept in the dark, at a temperature of 37° C., for 24 hours. After each hour an aliquot of specimen was taken. In the case of the plasma said amount was previously extracted with acetonitrile (1:2), "vortexed", and centrifuged at 3000 r.p.m. for 10 min. The supernatant was taken and used for analysis at HPLC with diode detector. The half-lives for the chemical stability and enzymatic stability were calculated by quantizing, in time, the percentage of pro-drug that remained in solution. A 1090L HPLC (Hewlett-Packard, Palo Alto, USA) coupled to a diode detector HP 1040A was used for the chromatographic separations. The column used was a Supelcosil LC-18, 250×4.6 mm, particle size 5 mm. The volume injected was 20 mL and the flow of 1 mL/min. The mobile phase was constituted by a mixture of aqueous $CH_3CN$/$H_3PO_4$ 1 mM (pH 3) [32:68]. For the quantitative determination reading was made at 250 nm. The retention times of the various compounds involved in the analysis were: for Flugal 6 min and for flurbiprofen 11 min. All the reagents and the solvents used were of analytical degree. The distilled and deionized water was purified by means of a Milli Q system (Millipore). The straight line of calibration for the quantification of the compounds was constructed using standard solutions with concentrations of between 0.1 and 100 μg/ml. Linearity was obtained with a coefficient of regression ($R^2$) of approximately 0.998. From the results of said analysis (illustrated in Table 3) it emerges that the pro-drug Flugal has a good chemical stability and a good susceptibility to enzymatic hydrolysis.

Chemical stability was assessed also at pH 1.0 in a solution of HCl 0.1N as described.

TABLE 3

Chemical stability and enzymatic stability of Flugal

| Compound | pH 1 T½ (hours) | pH 7.4 T½ (hours) | plasma T½ (hours) |
| --- | --- | --- | --- |
| Flugal | >8 | >8 | 1 |

Pharmacological Tests of Flugal

Test 1—Ulcerogenicity Studies

NSAID-induced gastric damage in mice was evaluated following the procedure described by Chan et al. (1995). In fasted (16-18 h) mice (n 6 per group), flurbiprofen free acid (10 mg/kg), flugal (16.3 mg/kg), or vehicle (CMC, 0.5%) was administered orally. After 4 h of treatment, mice were euthanized and the stomach was excised along its greater curvature and rinsed with normal saline. The mucosa was then examined by means of a magnifying glass for the presence of irritation or frank hemorrhagic lesions (ulcers). Irritation was assigned a score of 1, and ulcerations were scored according to their length (a score of 5 for lesions with a length between 1 and 3 mm; a score of 10 for lesions greater than 3 mm). The sum of total scores was used for comparison.

Flugal remarkably decreased ulcerogenic activity compared to flurbiprofen. Noteworthy, flugal caused only irritation without ulceration (Table 4). Thus, our results indicate that flugal remarkably reduced ulcerogenicity compared to flurbiprofen itself (Table 4).

TABLE 4

Ulcerogenic activity of flugal and flurbiprofen

| drugs | oral dose mg/kg | n. of ulcers | gastric lesion score |
| --- | --- | --- | --- |
| control | | 0 | |
| flurbiprofen | 10 | 3 ± 1.5 | 2 |
| flugal | 16.6 | 1 ± 1 | 0 |

Test 2-Anti-Inflammatory Activity.

The carrageenan induced mice hind paw oedema assay described by D'Agostino et al. (2007) was used to evaluate the acute anti-inflammatory activity of the conjugate. Mice were divided into control and test groups of six animals each. Initial paw volumes of all animals were measured using a plethysmometer apparatus (Ugo Basile, Milan, Italy) before treatment. Paw oedema was induced by a subplantar injection of 50 μL of saline containing 1% λ-carrageenan into the right hind paw. Flurbiprofen free acid and flugal were orally administrated 1 h before carrageenan challenge. Paw volume was measured at different time intervals by plethysmometer. The increase in paw volume was evaluated as the difference between the paw volume measured at each time point and the basal paw volume measured immediately before carrageenan injection.

As already reported in a previous characterization of this model (Posada et al., 2004) mouse paw oedema developed in two distinct phases: an acute first phase peaking at 4 h and a second phase peaking at 72 h after carrageenan challenge (FIG. 9 white-square). Flurbiprofen (10 mg/kg) significantly inhibited oedema formation until 48 h after carrageenan injection (FIG. 9 black-circle). On the other hand, equimolecular doses of flugal (16.3 mg/kg) did not modify carrageenan-induced oedema during first phase (0-6 h), while, it produced a significant anti-inflammatory effect during second phase (24-96 h), following carrageenan injection (FIG. 9 black-triangle). Control animals were treated with CMC, flurbiprofen and flugal 1 h before subplantar injection of carrageenan. Data are expressed as mean values (SEM of six animals for each group: (*) p<0.001; () p<0.01 versus control group).

Synthesis of the galactosylated derivative of acetylsalicylic acid (Asagal)

The galactosylated derivatives of acetylsalicylic acid (Asagal)

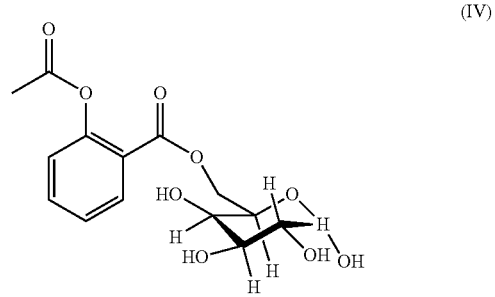

(IV)

is a pro-drug in which the drug is represented by acetylsalicylic acid and the vehicle by a galactose molecule.

Asagal is synthetized by esterifying the carboxyl group of acetylsalicylic acid with the hydroxyl in position 6' of galactose,

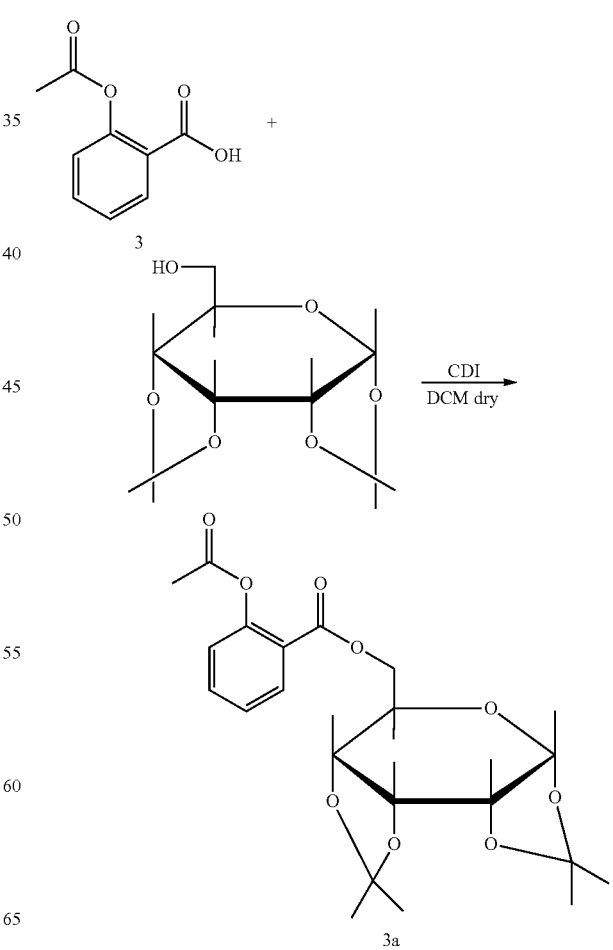

-continued

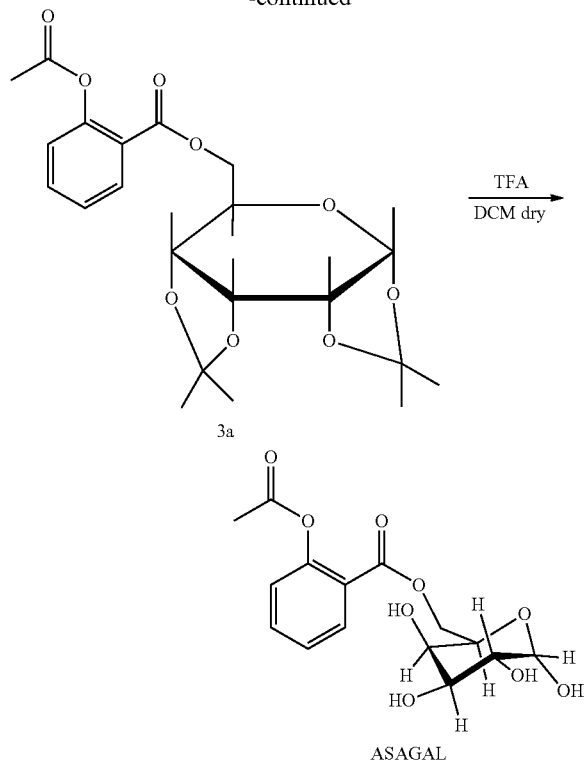

as given above and so far described for Ketogal and/or Flugal.
Chemical Part

Synthesis of diacetone
6'-O-acetylsalicylic-D-galactopyranoside (3a)

1 g of acetylsalicylic acid 3 (5.5 mmol), 1.43 g of 1,2,3,4-di-O-isopropylidene-D-α-galactopyranose (5.5 mmol), 1.08 g of 1-1' carbonyl di-imidazole (CDI) (6.6 mmol) were dissolved in anhydrous dichloromethane (10 mL). The reaction mixture was kept under electromagnetic stirring at room temperature for 12 hours. The organic phase was extracted several times with water and dehydrated with anhydrous sodium sulphate, filtered and dried in vacuo. The reaction crude was purified on a chromatography column with silica gel using $CHCl_3$ as eluent, to obtain 1.89 g of 3a as a white solid (yield 70%).

Synthesis of acetylsalicylic-D-galactos-6'-yl ester (Asagal)

Added to a solution of 3a (1.89 g; 3.8 mmol) in anhydrous dichloromethane (10 mL) were 2 mL of trifluoroacetic acid (TFA), and the reaction mixture was kept under electromagnetic stirring at room temperature for 48 hours. By evaporating the solvent, a residue was obtained, which was purified on a chromatography column with silica gel using $CHCl_3$ as eluent in a gradient of $CH_3OH$ to obtain 830 mg of Asagal as a white solid (yield 63%).

Synthetized for the first time in the present invention is a galactosylated derivative (Ketogal) of an non-steroidal anti-inflammatory (ketorolac). The process of blocking of an active drug in a pro form, by means of the esterification of the carboxyl group of the drug in question with the hydroxyl in position 6 of galactose, has enabled maintenance of the potent anti-inflammatory effect of the starting drug, on the other hand minimizing its negative effects.

The process of synthesis of the galactosylated derivatives has been repeated successfully for the creation of a second pro-drug (Flugal) and a third pro-drug (Asagal) derived from further non-steroidal anti-inflammatories (flurbiprofen and acetylsalicylic acid) in which the vehicle is always represented by a galactose molecule.

Various studies were conducted on chemical stability under physiological conditions (pH 7.4) and enzymatic stability (plasma) of the pro-drugs for verifying and testing their capacity for releasing the derivation drug.

In order to evaluate the anti-inflammatory, analgesic, and ulcerogenic activities of the pro-drug, numerous pharmacological analyses were conducted in which the results clearly highlight how the administration of Ketogal minimizes gastrointestinal toxicity, maintaining its anti-inflammatory and analgesic activity unaltered.

Furthermore, pharmacokinetic studies have highlighted how the galactosylated derivative of the non-steroidal anti-inflammatory produces a delayed and slower release, which is a fundamental process for the prevention of the formation of ulcers, a side effect common to all non-steroidal anti-inflammatories in so far as it has been shown how the administration of the pro-drug allows release of the drug into the blood plasma in therapeutic but non-toxic concentrations, as compared to the non-galactosylated form.

On the basis of these results, it may be stated that the synthesis of a galactosylated derivative of a non-steroidal anti-inflammatory forming the subject of the present invention enables minimization of gastrointestinal toxicity by means of esterification of the carboxyl group of the drug in question, preserving in any case the anti-inflammatory power and the analgesic activity of non-steroidal anti-inflammatories.

Synthesis of Okigal

The galactosylated derivative of ketoprofen (Okigal)

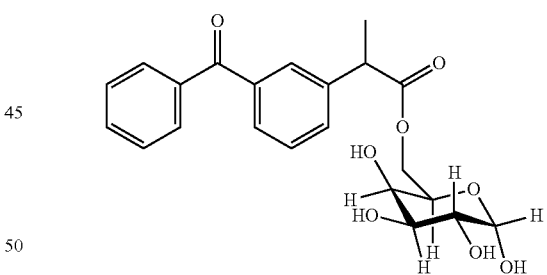

is a prodrug in which the drug is represented by ketoprofen

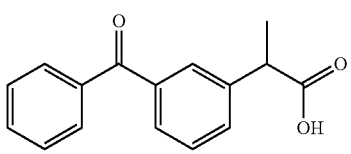

and the vehicle by a galactose molecule.

Okigal is synthesized by esterifying the carboxyl group of ketoprofen with the hydroxyl in position 6' of galactose, as described above for ketogal and flugal.

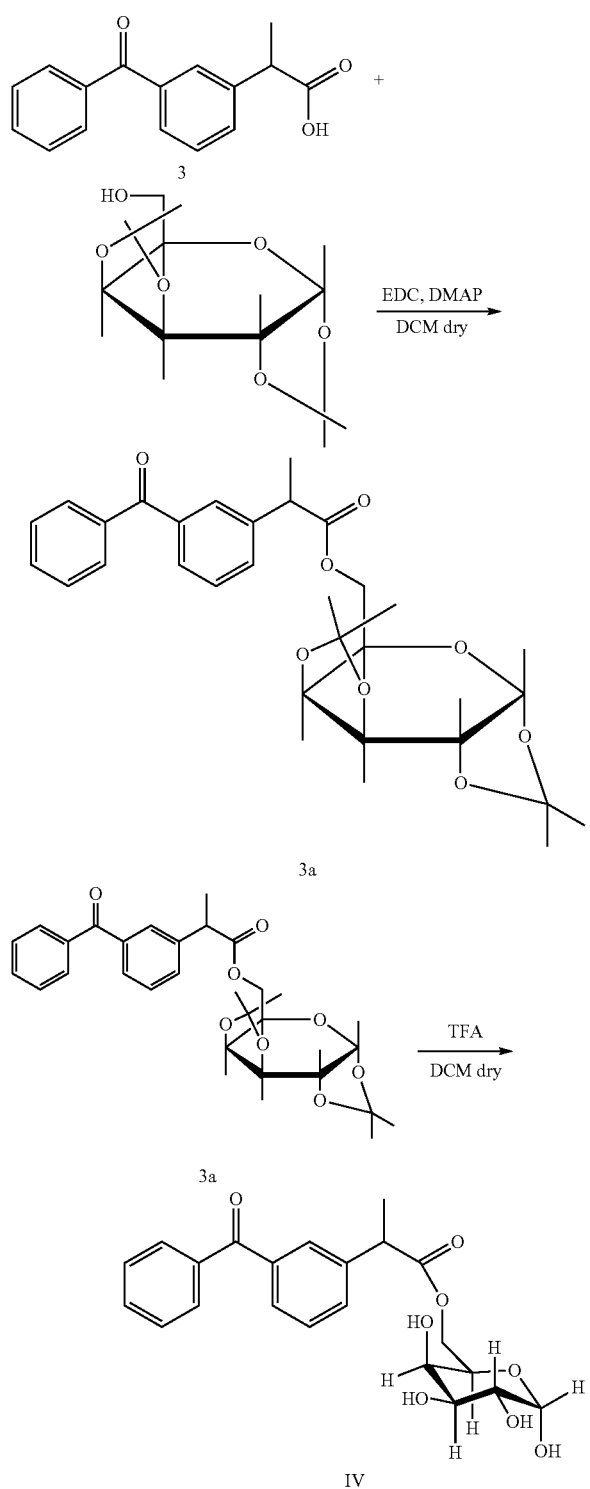

Chemical Part

Synthesis of Diacetone 6'-O-Ketoprofen-D-galactopyranoside (3a)

1 g of ketoprofen 3 (3.9 mmol), 1.014 g of 1,2,3,4-di-O-isopropylidene-D-α-galactopyranose (3.9 mmol), 747 mg of N-ethyl-N'-(3-dimethylaminopropyl)carbodiimide (EDC) HCl (3.9 mmol), and 24 mg of 4-(dimethyl amino)pyridine (DMAP) (0.195 mmol) were dissolved in anhydrous dichloromethane (10 mL). The reaction mixture was kept under electromagnetic stirring at room temperature for 12 hours. The organic phase was extracted several times with water and dehydrated with anhydrous sodium sulphate, filtered and dried in vacuo. The reaction crude was purified on a chromatography column with silica gel using $CH_2Cl_2$ as eluent, to obtain 990 mg of 3a as a white solid (yield 51%). m/z: 497 $(M+H)^+$.

Synthesis of Ketoprofen-D-galactos-6'-yl ester (Okigal—IV)

Added to a solution of 3a (0.99 g; 2.4 mmol) in anhydrous dichloromethane (10 mL) were 2 mL of trifluoroacetic acid (TFA), and the reaction mixture was kept under electromagnetic stirring at room temperature for 48 hours. By evaporating the solvent, a residue was obtained, which was purified on a chromatography column with silica gel using $CHCl_3$ as eluent in a gradient of $CH_3OH$ to obtain 550 mg of Okigal as a white solid (yield 55%). m/z: 417 $(M+H)^+$.

$^1$H-NMR ($CD_3OD$): δ 1.5 (d, 3H, —$CH_3$); 3.45 (m, 1H, 4'-H); 3.70 (m, 1H, —CH); 3.8 (m, 1H, 5'-H); 4.20 (m, 2H, 6'-H); 4.30 (m, 1H, 2'-H); 4.40 (m, 1H, 3'-H); 5.15 (m, 1H, 1'-H); 7.31 (m, 2H, 5"-H and 6"-H); 7.36 (m, 2H, 3'''-H and 5'''-H); 7.45 (m, 1H, 3-H, 4'''-H); 7.56 (s, 1-H, 2"-H); 7.7 (m, 2-H, 2'''-H and 6'''-H).

$^{13}$C-NMR ($CD_3OD$): δ 17 ($CH_3$); 40 (CH); 64 (C-6'); 68 (C-4'); 70 (C-5'); 73 (C-2'); 74 (C-3'); 93 and 98 (C-1'); 128 (C-3''' and C-5'''); 129 (C-4" and C-5"); 130 (C-2''' and C-6'''); 131 (C-2"); 132 (C-4'''); 133 (C-6"); 135 (C-1"); 139 (C-1''''); 140 (C-3"); 174 (CO-ester); 196 (CO-ketone).

Stability Studies of Okigal

For the stability study, the solutions of pro-drug were prepared by dissolving an aliquot of Okigal in a phosphate buffer at pH 7.4, or else in a solution of HCl 0.1 N (pH 1), as regards chemical stability, or else in a plasma specimen, for enzymatic stability. The solutions were kept in the dark, at a temperature of 37° C., for 24 hours. After each hour an aliquot of specimen was taken. In the case of plasma, said aliquot was previously extracted with acetonitrile (1:2), "vortexed" and centrifuged at 3000 r.p.m. for 10 min. The supernatant was taken and used for analysis at HPLC with diode detector. The half-lives for chemical stability and enzymatic stability were calculated by quantizing, in time, the percentage of pro-drug that remained in solution. For the chromatographic separations, a 1090L HPLC (Hewlett-Packard, Palo Alto, USA) was used, coupled to a diode detector HP 1040A. A Phenomenex Luna C18 (250×4.6 mm, 5 mm) column was used. The wavelength used was 250 nm. The mobile phase was constituted by acetonitrile and an aqueous solution of phosphoric acid 1 mm (pH 3) in the ratio of 32:68. The flow was 1 mL/min, with an injection volume of 20 μl. All the reagents and the solvents used were of analytical degree. The distilled and deionized water was purified by means of a Milli Q system (Millipore). The retention times of the compounds were: ketoprofen: 7 min; okigal: 9 min. The straight line of calibration for quantification of the compounds was constructed using standard solutions with concentrations of between 0.1 and 100 mg/ml. The 20 linearity was obtained with a coefficient of regression (R2) of approximately 0.998. From the results of said analysis (illustrated in Table 5) it emerges that the pro-drug okigal has a good chemical stability and a good susceptibility to enzymatic hydrolysis.

TABLE 5

Chemical stability and enzymatic stability of Okigal

| Compound | pH 1 T½ (hours) | pH 7.4 T½ (hours) | plasma T½ (hours) |
|---|---|---|---|
| Okigal | >8 | >8 | 4 |

Pharmacological Test of Ogikal
Test 1—Anti-Inflammatory Activity.

The carrageenan induced mice hind paw oedema assay described by D'Agostino et al. (2007) was used to evaluate the acute anti-inflammatory activity of the conjugate. Mice were divided into control and test groups of six animals each. Initial paw volumes of all animals were measured using a plethysmometer apparatus (Ugo Basile, Milan, Italy) before treatment. Paw oedema was induced by a subplantar injection of 50 μL of saline containing 1% λ-carrageenan into the right hind paw. Ketoprofen free acid and ketogal were orally administrated 1 h before carrageenan challenge. Paw volume was measured at different time intervals by plethysmometer. The increase in paw volume was evaluated as the difference between the paw volume measured at each time point and the basal paw volume measured immediately before carrageenan injection.

As already reported in a previous characterization of this model (Posada et al., 2004) mouse paw oedema developed in two distinct phases: an acute first phase peaking at 4 h and a second phase peaking at 72 h after carrageenan challenge (FIG. 10 white-circle). Ketoprofen (10 mg/kg) significantly inhibited oedema formation until 48 h after carrageenan injection (FIG. 1 black-square). On the other hand, equimolecular doses of okigal (16.3 mg/kg) slightly modify carrageenan-induced oedema during first phase (0-6 h), while, it produced a significant anti-inflammatory effect during second phase (24-96 h), following carrageenan injection (FIG. 10 black-triangle). Control animals were treated with CMC, ketoprofen and okigal 1 h before subplantar injection of carrageenan. Data are expressed as mean values (SEM of six animals for each group: (*) p<0.001; () p<0.01 versus control group).

REFERENCES

1. Brocks, D. R. and Jamali, F. Pharmacokinetics of ketorolac tromethamine. *Clin. Pharmacokin.* 1992, 23, 415-427.
2. Cioli, V.; Putzolu, S.; Rossi, V.; Barcellona, P. S.; Corradino, C. The role of direct tissue contact in the production of gastro-intestinal ulcers by anti-inflammatory drugs in rats. *Toxicol. Appl. Pharmacol.* 1979, 50, 283-289.
3. Rainsford, K. D. Mechanisms of gastrointestinal toxicity of non-steoridal anti-inflammatory drugs. *Scand. J. Gastroenterol.* 1989, *Suppl.* 163, 9-16
4. AIFA Bif XIV N.3 2007.

The invention claimed is:

1. A process of synthesis of galactosylated derivatives of a non-steroidal anti-inflammatory drug with free acid function, esterifying the carboxyl group with the hydroxyl in position 6 of galactose, using as condensing agent one of 1,1'-carbonyl di-imidazole (CDI) and N-ethyl-N'-(3-dimethyl amino-propyl)carbodiimide (EDC) HCl, with subsequent deprotection of the sugar using trifluoroacetic acid (TFA) in anhydrous dichloromethane, wherein said drug is ketorolac.

2. Pro-drugs of non-steroidal anti-inflammatory drugs with free acid function derivatized with an ester group, which have the general structural formula given below:

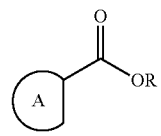

where A is and
where in the ester group R is a molecule of galactose conjugated in the 6' position.

3. Galactosylated derivatives of ketorolac having the following general structural formula:

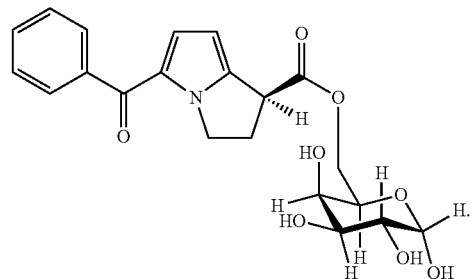

4. Pharmaceutical compositions with analgesic and anti-inflammatory activity comprising as active ingredient a derivative according to claim 3 in a mixture with an appropriate vehicle.

5. Pharmaceutical compositions with analgesic and anti-inflammatory activity comprising as active ingredient a conjugate according to claim 3 in a mixture with an appropriate vehicle.

6. A method for pain therapy or treating inflammatory diseases, comprising administering to a subject in need thereof an effective amount of a derivative according to claim 3.

7. A method for pain therapy or treating inflammatory diseases, comprising administering to a subject in need thereof an effective amount of a derivative according to claim 3.

8. Pharmaceutical compositions comprising the derivatives and/or the conjugates according to claim 3 in a technical form suitable for cutaneous, oral, sub-lingual, nasal, parenteral, rectal, intrathecal, bronchial, and intra-ocular administration.

9. The derivatives and/or conjugates according to claim 3 formulated as syrup, elixir, tablets, capsules, parenteral and injectable solutions, nasal solutions, collyria, powders, granulates, controlled-release capsules, emollient creams, ointments, impregnated bandages, controlled-release liposoluble plasters, or suppositories.

10. Pharmaceutical compositions with analgesic and anti-inflammatory activity comprising as active ingredient a conjugate or derivative according to claim 3 in a mixture with an excipient or vehicle for oral administration.

* * * * *

UNITED STATES PATENT AND TRADEMARK OFFICE
CERTIFICATE OF CORRECTION

PATENT NO. : 8,551,958 B2  Page 1 of 1
APPLICATION NO. : 13/015980
DATED : October 8, 2013
INVENTOR(S) : Maria Grazia Rimoli et al.

It is certified that error appears in the above-identified patent and that said Letters Patent is hereby corrected as shown below:

On the title page, please add Item (62) to read as follows:

Related U.S. Application Data

-- (62) Continuation-in-part of PCT/IT2009/000341 July 29, 2009 --

In the Claims:

Amend claim 2, column 18, line 12 to read as follows:

-- where A is ketorolac, and --

Signed and Sealed this
Twenty-eighth Day of January, 2014

Michelle K. Lee
*Deputy Director of the United States Patent and Trademark Office*